United States Patent
Ahmed et al.

(10) Patent No.: US 7,960,418 B2
(45) Date of Patent: Jun. 14, 2011

(54) 4β-AMINO PODOPHYLLOTOXIN CONGENERS AS POTENTIAL ANTICANCER AGENTS AND A PROCESS FOR THE PREPARATION THEREOF

(75) Inventors: Kamal Ahmed, Hyderabad (IN); Ashwini Kumar Banala, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 234 days.

(21) Appl. No.: 12/112,637

(22) Filed: Apr. 30, 2008

(65) Prior Publication Data
US 2008/0275248 A1    Nov. 6, 2008

(30) Foreign Application Priority Data
May 3, 2007  (IN) .............................. 953/DEL/2007

(51) Int. Cl.
*C07F 9/28*  (2006.01)
*A01N 43/78*  (2006.01)
(52) U.S. Cl. ....................... 514/367; 548/117
(58) Field of Classification Search .................. None
See application file for complete search history.

(56) References Cited

OTHER PUBLICATIONS

Fischer et al., Cancer Treatment Reviews 2007, 33, 391-406.*
Sarcoma, http://en.wikipedia.org/wiki/HT1080, 2010.*
Non-smallCell, http://dtp.nci.nih.ogv/docs/misc/common_files/cell_list.html (2010).*

* cited by examiner

*Primary Examiner* — Sun Jae Y Loewe
(74) *Attorney, Agent, or Firm* — K&L Gates LLP

(57) ABSTRACT

The present invention provides new class of 4β-[4"-(1",3"-benzothiazole-2"-yl)anilino]podophyllotoxin analogues having the structural formula as follows (4).

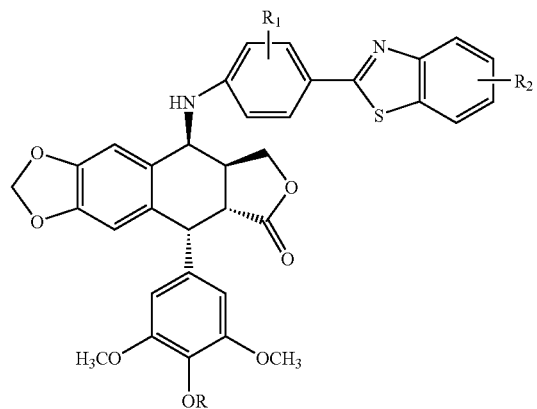

Where R=H or $CH_3$; $R_1$=H, halogen, $CH_3$ and $R_2$=H, halogen, $OCH_3$.

The present invention also provides a process for the preparation of new 4β-[4"-(1", 3"-benzothiazole-2"-yl)anilino] podophyllotoxin analogues as useful anticancer agents. More particularly, it provides a process for the preparation of 4β-[4"-(1",3"-benzothiazole-2"-yl)anilino] derivatives of podophyllotoxin. The process for the synthesis of new podophyllotoxin analogues as anticancer agents produces the novel and stereo-selective derivatives of the podophyllotoxin in good yields, where in the key step for the synthesis of these analogues is by direct nucleophilic substitution of C-4β-iodo intermediates. The 4β-iodopodophyllotoxin, which has been reacted with substituted or unsubstituted 4-(1,3-benzothiazole-2-yl)aniline in a stereo-selective manner to afford the 4β-[4"-(1",3"-benzothiazole-2"-yl)anilino] derivatives of podophyllotoxin.

9 Claims, No Drawings

4β-AMINO PODOPHYLLOTOXIN CONGENERS AS POTENTIAL ANTICANCER AGENTS AND A PROCESS FOR THE PREPARATION THEREOF

FIELD OF THE INVENTION

The present invention relates to a process for the synthesis of novel 4β-amino podophyllotoxin congeners as antitumour antibiotics. More particularly, the present invention relates to the synthesis of a novel class of 4β-amino derivatives of the podophyllotoxin as useful anticancer or antitumour agents.

BACKGROUND OF THE INVENTION

Etoposide and teniposide are semi-synthetic podophyllotoxin derivatives that are in clinical usage as anticancer drugs FIG. 1 (Chen. Y. Z.; Wang. Y. G.; Tian, X.; Li, J. X. *Curr. Sci* 1990, 59, 517.; Wang, J. Z.; Tian, X.; Tsumura, H.; Shimura, K.; Ito, H. *Anti-cancer Drug Design,* 1993, 8, 193). It is believed that analogues of 4'-demethyl epipodophyllotoxin exert their antitumour activity through stabilization of a cleavable complex between DNA and type II DNA topoisomerase, this leads ultimately to inhibition of DNA catenation activity and produces single and double strand breaks (Satio, H.; Yoshikawa, H.; Nishimura, Y.; Kondo, S.; Takeuchi, T.; Umezawa, H. *Chem Pharm. Bull.* 1986, 34, 3733.; Chen, Y. Z.; Wang, Y. G.; Li, J. X.; Tian, X.; Jia. Z. P.; Zhang, Z. Y. *Life Sci.* 1989, 45, 2569) A number of studies have been carried out on the structural modification of glycoside by amino substituents that has improved the inhibitory activity on human DNA topoisomerase II as well as stronger activity in causing cellular protein length DNA breakage (Lee, K. H.; Imakura, Y.; Haruna, M.; Beers, S. A.; Thurston, L. S.; Dai, H. J.; Chen, C. H.; Liu, S. Y.; Cheng, Y. C. *J. Nat. Prod.* 1989, 52, 606.; Liu, S. Y.; Hawang, B. D.; Haruna, M.; Imakura, Y.; Lee, K. H.; Cheng, Y. C. *Mol. Pharmcol.* 1989, 36, 8.; Lee, K, H.; Beers, S. A.; Mori, M.; Wang, Z. Q.; Kuo, Y. H.; Li, L.; Liu, S. Y.; Cheng, Y. C.; *J. Med. Chem.* 1990, 33, 1364.; Kamal, A.; Gayatri, N. L.; Reddy, D. R.; Reddy, P. S. M. M.; Arifuddin, M.; Dastidar, S. G.; Kondapi, M. A.; Rajkumar M. *Bioorg. Med. Chem.* 2005, 13, 6218; Kamal, A.; Kumar, B. A.; Arifuddin, M.; Dastidar, S. G. *Bioorg. Med. Chem.* 2003, 11, 5135). In this context a large number of 4β-amino derivatives of podophyllotoxin and 4'-O-demethyl epipodophyllotoxin based compounds have been synthesized and investigated for their antitumour activity.

Figure-1

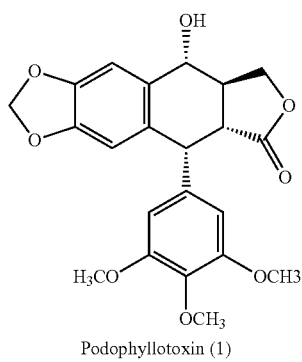

Podophyllotoxin (1)

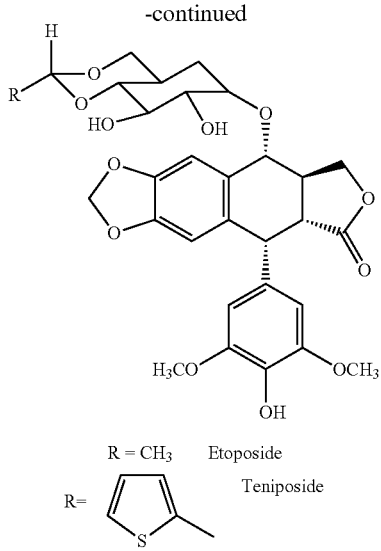

R = CH₃  Etoposide
R = (thiophene)  Teniposide

OBJECTIVE OF THE INVENTION

The main object of the invention is to provide the new 4β-amino podophyllotoxin congeners as useful antitumour antibiotics.

Another object of the present invention is to provide a process for the synthesis of these new 4β-amino derivatives of podophyllotoxin as useful anticancer or antitumour agents.

Another object of the present invention is to provide new and stereoselective compounds based on the podophyllotoxin and 4'-O-demethylepipodophyllotoxin in good yields.

SUMMARY OF THE INVENTION

Accordingly the present invention provides a novel podophyllotoxin of general formula 4

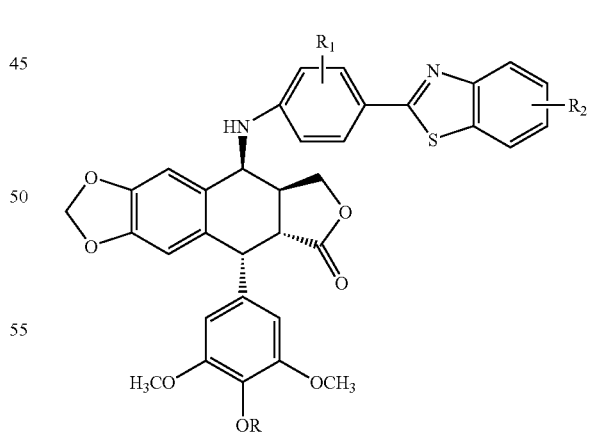

wherein R=H or CH₃; $R_1$ is selected from H, halogen and CH₃, and $R_2$ is selected from H, halogen and OCH₃.

In an embodiment of the present invention the representative compounds of podophyllotoxin of general formula 4 are as follows:

4β-[4"-(1",3"-benzothiazole-2"-yl)anilino]-4-desoxypodophyllotoxin (4a);

4'-O-Demethyl-4β-[4''-(1'',3''-benzothiazole-2''-yl)anilino]-4-desoxy podophyllotoxin (4b);
4β-[4''-(1'',3''-Benzothiazole-2''-yl)-3''-chloroanilino]-4-desoxypodophyllotoxin (4c);
4'-O-Demethyl-4β-[4''-(1'',3''-benzothiazole-2''-yl)-3''-chloroanilino]-4-desoxy podophyllotoxin (4d);
4β-[4''-(6''-Methoxy-1'',3''-benzothiazole-2''-yl)anilino]-4-desoxypodophyllotoxin (4e);
4'-O-Demethyl-4β-[4''-(6''-methoxy-1'',3''-benzothiazole-2''-yl)anilino]-4-desoxy podophyllotoxin (4f);
4β-[4''-(6''-Fluoro-1'',3''-benzothiazole-2''-yl)anilino]-4-desoxypodophyllotoxin (4g);
4'-O-Demethyl-4β-[4''-(6''-fluoro-1'',3''-benzothiazole-2''-yl)anilino]-4-desoxy podophyllotoxin (4h);
4β-[4''-(4''-Chloro-1'',3''-benzothiazole-2''-yl)anilino]-4-desoxypodophyllotoxin (4i);
4'-O-Demethyl-4β-[4''-(4''-chloro-1'',3''-benzothiazole-2''-yl)anilino]-4-desoxy podophyllotoxin (4j);
4β-[4''-(4'',6''-Dichloro-1'',3''-benzothiazole-2''-yl)anilino]-4-desoxypodophyllotoxin (4k);
4'-O-Demethyl-4β-[4''-(4'',6''-dichloro-1'',3''-benzothiazole-2''-yl)anilino]-4-desoxy podophyllotoxin (4l);
4β-[4''-(1'',3''-Benzothiazole-2''-yl)-2''-bromoanilino]-4-desoxypodophyllotoxin (4m);
4'-O-Demethyl-4β-[4''-(1'',3''-benzothiazole-2''-yl)-2-bromoanilino]-4-desoxypodophyllotoxin (4n);
4β-[4''-(1'',3''-Benzothiazole-2''-yl)-2''-methylanilino]-4-desoxypodophyllotoxin (4o) and
4'-O-Demethyl-4β-[4''-(1'',3''-benzothiazole-2''-yl)-2''-methylanilino]-4-desoxy podophyllotoxin (4p).

In yet another embodiment, the general structures of the representative compounds of podophyllotoxin of formula 4 are as follows:

4a
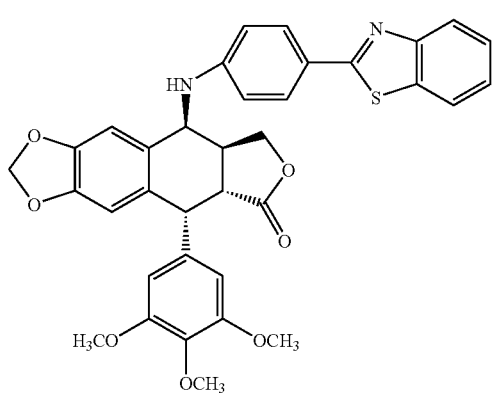

4b
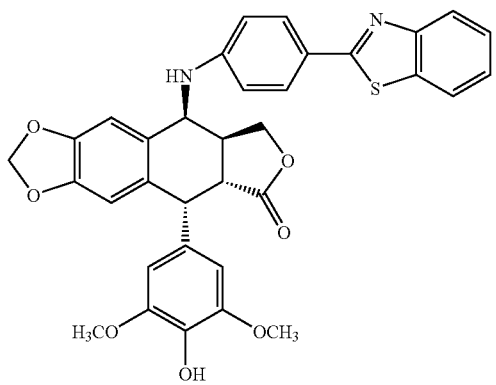

4c
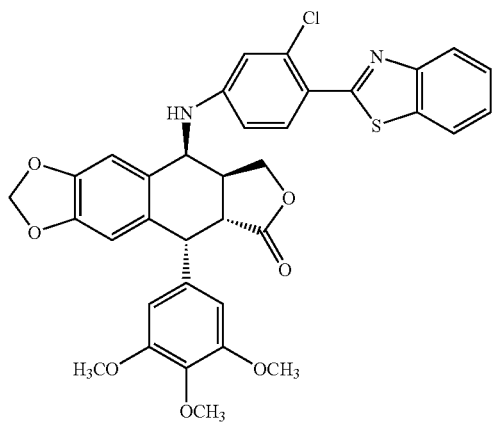

4d
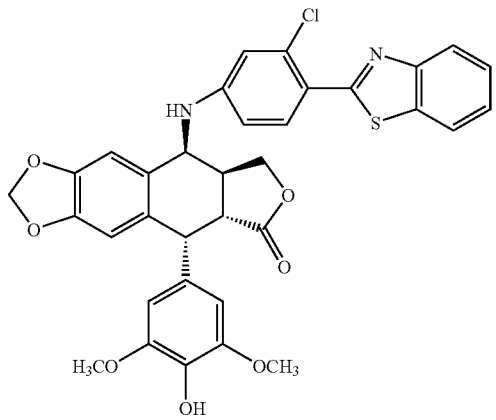

4e
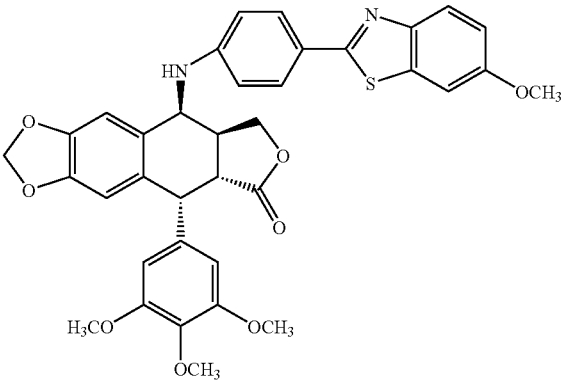

4f
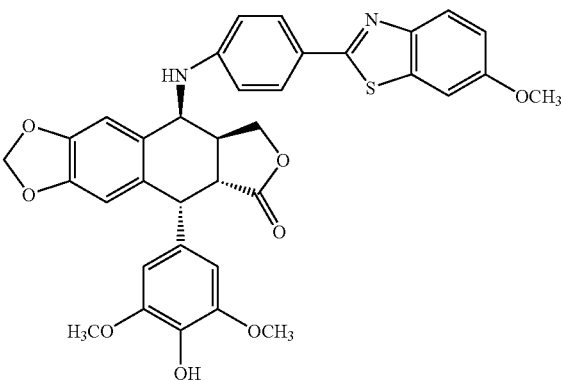

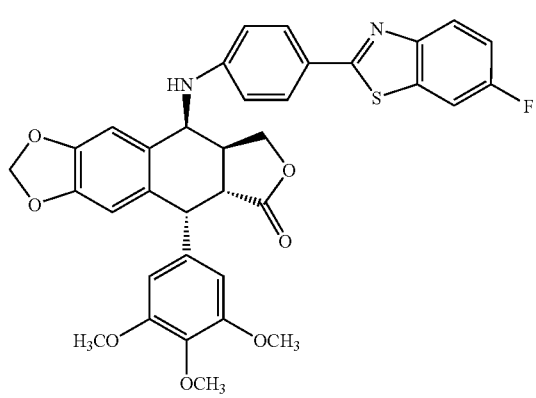
4g
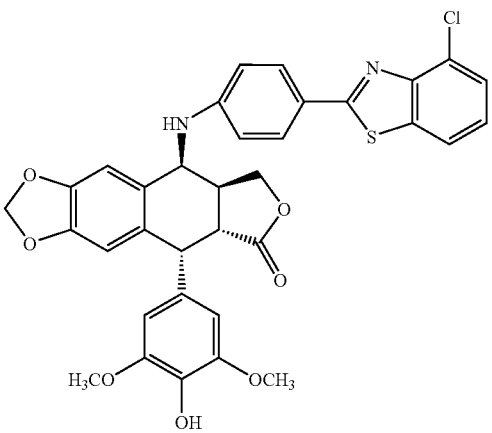
4j
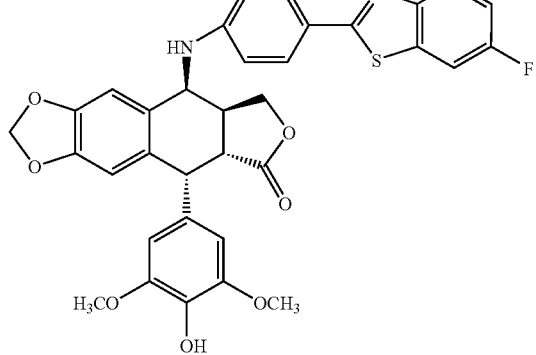
4h
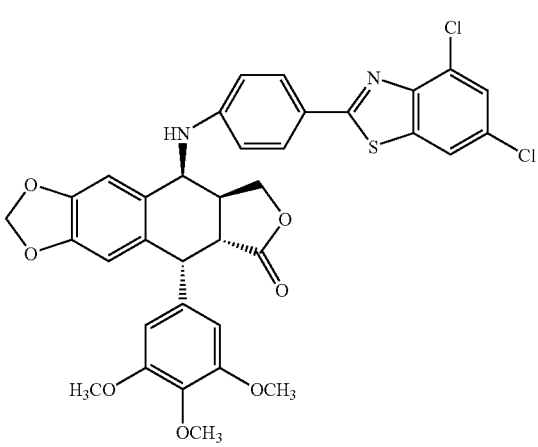
4k
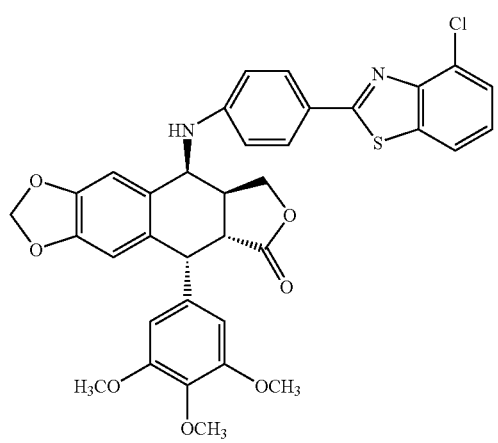
4i
4l

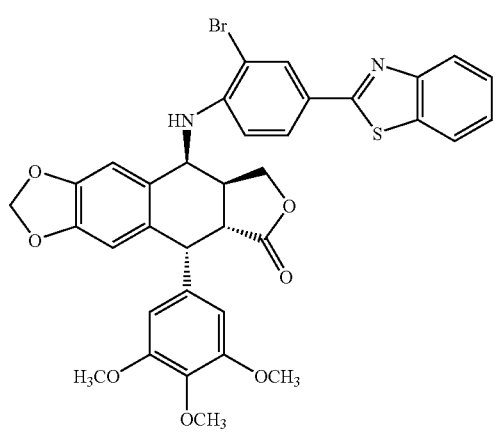

4m

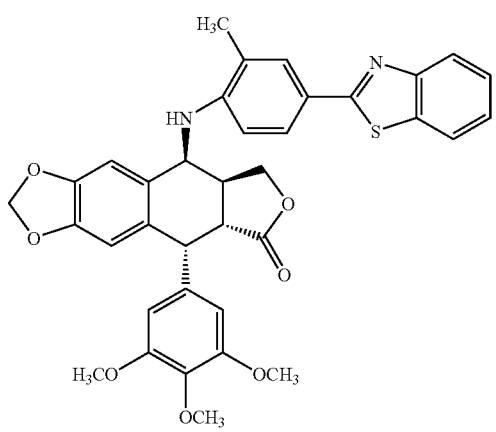

4o

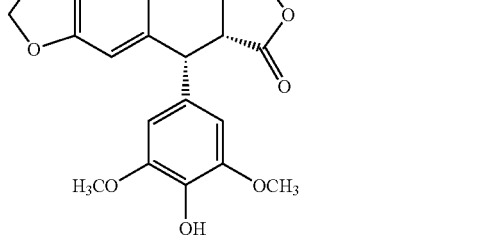

4p

4n

In yet another embodiment the novel podophyllotoxin of formula 4 exhibits in vitro anticancer activity against human cell lines.

In yet another embodiment the human cancer lines used are derived from the cancer type selected from the group consisting of colon (Colo205), lung (Hop-62), cervix (SiHa), prostate (DU145, PC3), oral (DWD, HT1080), and breast (MCF7, Zr-75-1).

In yet another embodiment the novel podophyllotoxin exhibits the following Cytotoxicity (in vitro) data for some representative compounds towards cancer cell lines compared to the standard drug tested with the concentration that produced 50% inhibition of cell growth ($IC_{50}$)

| | Activity status in terms of $IC_{50}$ values (µg/ml) | | | | | | | | |
|---|---|---|---|---|---|---|---|---|---|
| | Colon | Prostate | | Lung | Breast | | Cervix | Oral | |
| Compd. | Colo205 | DU145 | PC3 | Hop62 | MCF7 | Zr-75-1 | SiHa | HT1080 | DWD |
| 4a | 8 | >80 | >80 | >80 | >80 | >80 | >80 | 8 | 22 |
| 4b | 8 | 13 | >80 | 8 | >80 | >80 | >80 | >80 | 6 |
| 4c | 7 | >80 | >80 | 15 | >80 | >80 | >80 | 9 | 5 |
| 4d | 7 | >80 | >80 | 60 | >80 | >80 | >80 | 9 | 7 |
| 4g | 7 | >80 | >80 | 30 | >80 | >80 | >80 | 9 | 5 |
| 4h | 8 | >80 | >80 | 10 | >80 | >80 | >80 | >80 | 9 |
| ADR | 5 | 6 | 5 | 5 | 5 | 5 | 5 | 4 | 2 |
| 1 | 5 | 2 | 8 | 13 | 3 | 7 | 23 | 8 | 6 |

The present invention further provides a process for the preparation of novel podophyllotoxin of general formula 4.

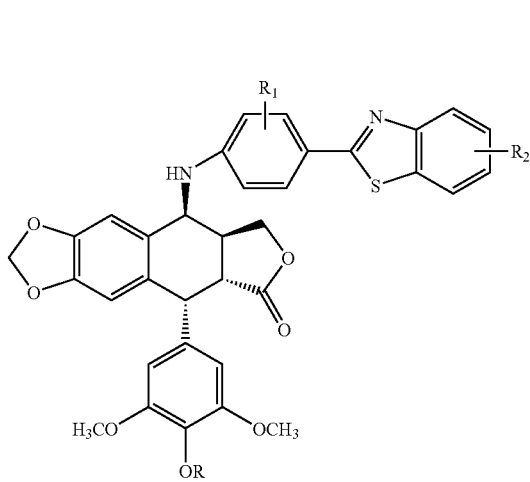

4 wherein R=H or CH$_3$; R$_1$ is selected from H, halogen and CH$_3$ and R$_2$ is selected from H, halogen and OCH$_3$ and said process comprising the steps of:
a) adding sodium iodide to solution of podophyllotoxin in a solvent selected from the group consisting of dry acetonitrile, dry dichloromethane (DCM), dimethylformamide (DMF) and mixtures thereof, under stirring, for 5-10 min,
b) adding dropwise methanesulphonic acid to the reaction mixture obtained in step (a), under stirring, at a temperature of about 0° C. and continuing the stirring for 0.5-5 hrs, at a temperature in the range of 20-30° C., bubbling the resultant reaction mixture with nitrogen to remove the excess of hydrogen iodide, followed by evaporation to obtain the resultant crude product,
c) adding anhydrous barium carbonate and the compound of general formula 3

3 wherein R$_1$ is selected from H, halogen and CH$_3$ and R$_2$ is selected from H, halogen and OCH$_3$ in dry tetrahydrofuran (THF) to the crude product obtained in step (b), under stirring, for 6-9 hrs, at a temperature in the range of 20-30° C., under nitrogen, followed by purification by known method to obtain the desired product.

In an embodiment of the present invention the compound of general formula 3 used is selected from the group consisting of 4-(1,3-benzothiazole-2-yl)aniline, 4-(1,3-benzothiazole-2yl)-3-chloroaniline, 4-(6-methoxy-1,3-benzothiazole-2-yl)aniline, 4-(6-fluoro-1,3-benzothiazole-2-yl)aniline, 4-(4-chloro-1,3-benzothiazile-2-yl)aniline, 4-(4,6-dichloro-1,3-benzothiazole-2-yl)aniline, 4-(1,3-benzothiazole-2-yl)-2-bromoaniline and 4-(1,3-benzothiazole-2-yl)-2-methylaniline.

DETAILED DESCRIPTION

Accordingly, the present invention provides new class of 4β-[4"-(1",3"-benzothiazole-2"-yl)anilino]podophyllotoxin analogues having the structural formula (4) as follows:

4 where R=H or CH$_3$; R$_1$=H, halogen, CH$_3$ and R$_2$=H, halogen, OCH$_3$.

The present invention also provides a process for the preparation of new 4β-[4"-(1", 3"-benzothiazole-2"-yl)anilino] podophyllotoxin analogues as useful anticancer agents. More particularly, it provides a process for the preparation of 4β-[4"-(1",3"-benzothiazole-2"-yl)anilino] derivatives of podophyllotoxin.

The process for the synthesis of new podophyllotoxin analogues as anticancer agents produces the novel and stereoselective derivatives of the podophyllotoxin in good yields, where in the key step for the synthesis of these analogues is by direct nucleophilic substitution of C-4β-iodo intermediates. The 4β-iodopodophyllotoxin, which has been reacted with substituted or unsubstituted 4-(1,3-benzothiazole-2-yl) aniline in a stereo-selective manner to afford the 4β-[4"-(1", 3"-benzothiazole-2"-yl)anilino] derivatives of podophyllotoxin.

These 4-iodopodophyllotoxin intermediates have been prepared by the iodination of the related podophyllotoxin compounds as described in the literature (Kamal, A.; Laxman, N.; Ramesh. G. *Bioorg. Med. Chem. Lett.* 2000, 10, 2059.).

In the present invention, the naturally occurring podophyllotoxin lignan was isolated from *Podophyllum peltatum linnaeus*.

The synthesis of 4β-intermediates have been carried out from iodination of podophyllotoxin.

In yet another embodiment of the present invention 1-2 eq. of different unsubstituted and substituted 4-(1,3-benzothiazole-2-yl)aniline compounds have been used.

In still another embodiment of the present invention a variety of solvents were used for the nucleophilic substitution step, such as dichloromethane, chloroform and tetrahydrofuran.

In still another embodiment of the present invention bases like K$_2$CO$_3$, Et$_3$N were used.

In still another embodiment of the present invention the purification of these analogues was done by column chromatography employing ethylacetate/hexane as eluent.

Thus the present invention provides new class of podophyllotoxin analogues, which were synthesized in a stereoselective manner.

A program was initiated in the laboratory for the design and synthesis of new 4β-aryl amino substituted podophyllotoxin congeners with enhanced antitumour activity and/or activity against etoposide resistant tumor cell lines. In these efforts new 4β-[4"-(1",3"-benzothiazole-2"-yl)anilino] derivatives of podophyllotoxin have been synthesized and evaluated for their cytotoxicity and anticancer potency compared to adiramycin. The synthesis of these compounds has been carried out as described in the Scheme 1 using podophyllotoxin obtained from the resin.

Some of the compounds of the present invention are given below:

a) 4β-[4"-(1",3"-Benzothiazole-2"-yl)anilino]-4-desoxypodophyllotoxin
b) 4'-O-Demethyl-4β-[4"-(1",3"-benzothiazole-2"-yl)anilino]-4-desoxypodophyllotoxin
c) 4β-[4"-(1",3"-Benzothiazole-2"-yl)-3"-chloroanilino]-4-desoxypodophyllotoxin
d) 4'-O-Demethyl-4β-[4"-(1",3"-benzothiazole-2"-yl)-3"-chloroanilino]-4-desoxypodophyllotoxin
e) 4β-[4"-(6"-Methoxy-1",3"-benzothiazole-2"-yl)anilino]-4-desoxypodophyllotoxin
f) 4'-O-Demethyl-4β-[4"-(6"-methoxy-1",3"-benzothiazole-2"-yl)anilino]-4-desoxypodophyllotoxin
g) 4β-[4"-(6"-Fluoro-1",3"-benzothiazole-2"-yl)anilino]-4-desoxypodophyllotoxin
h) 4'-O-Demethyl-4β-[4"-(6"-fluoro-1",3"-benzothiazole-2"-yl)anilino]-4-desoxypodophyllotoxin
i) 4β-[4"-(4"-Chloro-1",3"-benzothiazole-2"-yl)anilino]-4-desoxypodophyllotoxin
j) 4'-O-Demethyl-4β-[4"-(4"-chloro-1",3"-benzothiazole-2"-yl)anilino]-4-desoxypodophyllotoxin
k) 4β-[4"-(4",6"-Dichloro-1",3"-benzothiazole-2"-yl)anilino]-4-desoxypodophyllotoxin
l) 4'-O-Demethyl-4β-[4"-(4",6"-dichloro-1",3"-benzothiazole-2"-yl)anilino]-4-desoxypodophyllotoxin
m) 4β-[4"-(1",3"-Benzothiazole-2"-yl)-2"-bromoanilino]-4-desoxypodophyllotoxin
n) 4'-O-Demethyl-4β-[4"-(1",3"-benzothiazole-2"-yl)-2"-bromoanilino]-4-desoxypodophyllotoxin
o) 4β-[4"-(1",3"-Benzothiazole-2"-yl)-2"-methylanilino]-4-desoxypodophyllotoxin
p) 4'-O-Demethyl-4β-[4"-(1",3"-benzothiazole-2"-yl)-2"-methylanilino]-4-desoxypodophyllotoxin The following examples are given by the way of illustration and therefore should not be construed to limit the scope of the invention

EXAMPLE 1

4β-[4"-(1",3"-benzothiazole-2"-yl)anilino]-4-desoxypodophyllotoxin (4a)

To a solution of podophyllotoxin (414 mg, 1 mmol) in dry acetonitrile (10 ml), sodium iodide (298 mg, 2 mmol) was added and stirred for 5 min. To this stirred reaction mixture, methanesulphonic acid (0.13 ml, 2 mmol) was added dropwise at 0° C. and the stirring was continued for another 0.5 h at room temperature. Nitrogen was bubbled through the solution to drive of the excess hydrogen iodide. This solution was then evaporated in vacuo and used for the next reaction without further purification. To the crude product, anhydrous barium carbonate (395 mg, 2 mmol) and 4-(1,3-benzothiazole-2-yl)aniline (271 mg, 1.2 mmol) in 10 ml of dry tetrahydrofuran under nitrogen was added and stirred for 8 h at room temperature. Reaction mixture was dried and purified via column chromatography using ethylacetate/hexane mixture as eluent to get pure product in 80% yield.

m.p: 172-175° C. $[\alpha]_D$: -120.00
$^1$H-NMR(CDCl$_3$): δ 3.04 (m, 2H), 3.77 (s, 6H), 3.8 (s, 3H), 3.97 (t, 1H, J=9.66 Hz), 4.40 (m, 2H), 4.55 (d, 1H, J=4.46 Hz), 4.76 (m, 1H), 5.96 (d, 2H, J=4.7 Hz), 6.27 (s, 2H), 6.52 (s, 1H), 6.63 (d, 2H, J=8.17 Hz), 6.8 (s, 1H), 7.32 (t, 1H, J=7.43 Hz), 7.44 (t, 1H, J=7.43 Hz), 7.84 (d, 1H, J=8.17 Hz), 7.96 (m, 3H).
IR(KBr)cm$^{-1}$: 3362, 2925, 1772, 1604.
MS (FAB): 622 [M$^+$].

EXAMPLE 2

4'-O-Demethyl-4β-[4"-(1",3"-benzothiazole-2"-yl)anilino]-4-desoxypodophyllotoxin (4b)

To a solution of podophyllotoxin (414 mg, 1 mmol) in dry DCM (10 ml), sodium iodide (298 mg, 2 mmol) was added and stirred for 5 min. To this stirred reaction mixture, methanesulphonic acid (0.13 ml, 2 mmol) was added dropwise at 0° C. and the stirring was continued for another 5 h at room temperature. Nitrogen was bubbled through the solution to drive of the excess hydrogen iodide. This solution was then evaporated in vacuo and used for the next reaction without further purification. To the above crude product, anhydrous barium carbonate (395 mg, 2 mmol) and 4-(1,3-benzothiazole-2-yl)aniline (271 mg, 1.2 mmol) in 10 ml of dry tetrahydrofuran under nitrogen was added and stirred for 8 h at room temperature. The reaction mixture was dried and purified via column chromatography using ethylacetate, hexane mixture as eluent to get pure product in 55% yield.

m.p: 143-147° C. $[\alpha]_D$: -116.0
$^1$H-NMR(CDCl$_3$): δ 3.04 (m, 1H), 3.28 (dd, 1H, J=14.37, 4.49 Hz), 3.76 (s, 6H), 3.88 (m, 2H), 4.34 (t, 1H, J=8.98 Hz), 4.53(d, 1H, J=4.5 Hz), 4.85(br, 1H), 5.95 (d, 2H), J=4.6 Hz), 6.28(s, 2H), 6.50 (s, 1H), 6.72 (d, 2H, J=8.98 Hz), 6.8 (s, 1H), 7.28 (t, 1H, J=7.18 Hz), 7.4 (t, 1H, J=7.18 Hz), 7.84 (m, 4H).
IR(KBr)cm$^{-1}$: 3392, 2914, 1773, 1610.
MS (FAB): 608 [M$^+$].

EXAMPLE 3

4β-[4"-(1",3"-Benzothiazole-2"-yl)-3"-chloroanilino]-4-desoxypodophyllotoxin (4c)

This compound was prepared according to the method described for 4a employing 4-(1,3-benzothiazole-2yl)-3-chloroaniline (312 mg, 1.2 mmol) and podophyllotoxin (414 mg, 1 mmol) to get pure product in 75% yield.

m.p: 156-160° C. $[\alpha]_D$: -122.0
$^1$H-NMR(CDCl$_3$): δ 2.93 (m, 2H), 3.73 (s, 3H), 3.76 (s, 6H), 3.94 (t, 1H, J=9.06 Hz), 4.38 (t, 2H, J=7.55 Hz), 4.45 (m, 1H), 4.72 (m, 1H), 5.85 (s, 1H), 5.93 (s, 1H), 6.23 (s, 2H), 6.46 (s, 1H), 6.6 (d, 1H, J=8.31 Hz), 6.7 (s, 1H), 6.75 (s, 1H), 7.34 (t, 1H, J=8.31 Hz), 7.45 (t, 1H, J=8.31 Hz), 7.87 (d, 1H, J=7.554 Hz), 7.98 (d, 1H, J=8.31 Hz), 8.21 (d, 1H, J=8.31 Hz).
IR(KBr)cm$^{-1}$: 3398, 2924, 1771, 1615.
MS (FAB): 657 [M$^+$].

EXAMPLE 4

4'-O-Demethyl-4β-[4"-(1",3"-benzothiazole-2"-yl)-3"-chloroanilino]-4-desoxypodophyllotoxin (4d)

This compound was prepared according to the method described for 4b employing 4-(1,3-benzothiazole-2yl)-3-chloroaniline (312 mg, 1.2 mmol) and podophyllotoxin (414 mg, 1 mmol) to get pure product in 60% yield.

m.p: 157-160° C. $[\alpha]_D$: -124.0

¹H-NMR(CDCl₃): δ 3.02 (m, 2H), 3.8 (s, 6H), 4.4 (m, 2H), 4.55 (m, 1H), 4.75 (m, 1H,), 5.40 (br, 1H), 5.85 (s, 1H), 5.98 and 5.93 (ABq, 2H, J=1.51), 6.29 (s, 2H), 6.51 (s, 1H), 6.6 (dd, 1H, J=9.06, 2.26 Hz), 6.69 (d, 1H, J=2.26 Hz), 6.77 (s, 1H), 7.37 (t, 1H, J=8.31), 7.48 (t, 1H, J=8.31 Hz), 7.9 (d, 1H, J=7.55 Hz), 8.03 (d, 1H, J=7.55 Hz), 8.22 (d, 1H, J=9.06 Hz).
IR(KBr)cm⁻¹: 3395, 2920, 1772, 1607.
MS (FAB): 643 [M⁺].

EXAMPLE 5

4β-[4"-(6"-Methoxy-1",3"-benzothiazole-2"-yl)anilino]-4-desoxypodophyllotoxin (4e)

This compound was prepared according to the method described for 4a employing 4-(6-methoxy-1,3-benzothiazole-2-yl)aniline (307 mg, 1.2 mmol) and podophyllotoxin (414 mg, 1 mmol) to get pure product in 75% yield.
m.p: 102-105° C. [α]$_D$: −85.0
¹H-NMR(CDCl₃):δ3.0 (m, 2H), 3.75 (s, 6H), 3.78 (s, 3H), 3.87 (s, 3H), 4.39 (m, 2H), 4.51(d, 1H, J=3.77 Hz), 4.73 (m, 1H), 5.92 and 5.95 (ABq, 2H, J=1.51 Hz), 6.25 (s, 2H), 6.48 (s, 1H), 6.60 (d, 2H, J=8.31), 6.77 (s, 1H), 7.0 (dd, 1H, J=9.07, 2.26 Hz), 7.28 (d, 1H, J=2.26 Hz), 7.80-7.88 (m, 3H).
IR(KBr)cm⁻¹: 3366, 2924, 2853, 1772, 1606.
MS (FAB): 652 [M⁺].

EXAMPLE 6

4'-O-Demethyl-4β-[4"-(6"-methoxy-1",3"-benzothiazole-2"-yl)anilino]-4-desoxypodophyllotoxin (4f)

This compound was prepared according to the method described for 4b employing 4-(6-methoxy-1,3-benzothiazole-2-yl)aniline (307mg, 1.2 mmol) and podophyllotoxin (414 mg, 1 mmol) to get pure product in 58% yield.
m.p: 142-146° C. [α]$_D$: −109.0
¹H-NMR(CDCl₃): δ 3.06 (m, 2H), 3.80 (s, 6H), 3.89 (s, 3H), 4.35 (m, 2H), 4.6 (d, 1H, J=4.01 Hz), 4.77 (m, 1H), 5.4 (br, 1H), 5.95 (s, 1H), 5.98 (s, 1H), 6.3(s, 2H), 6.52 (s, 1H), 6.61 (d, 2H, J=8.82 Hz), 6.79 (s, 1H), 7.02 (dd, 1H, J=9.22, 2.41 Hz), 7.31 (d, 1H, J=2.41 Hz), 7.82-7.91 (m, 3H).
IR(KBr)cm⁻¹: 3367, 2922, 1771, 1605.
MS (FAB): 638 [M⁺].

EXAMPLE 7

4β-[4"-(6"-Fluoro-1",3"-benzothiazole-2"-yl)anilino]-4-desoxypodophyllotoxin (4g)

This compound was prepared according to the method described for 4a employing 4-(6-fluoro-1,3-benzothiazole-2-yl)aniline(293 mg, 1.2 mmol) and podophyllotoxin (414 mg, 1 mmol) to get pure product in 75% yield.
m.p: 168-172° C. [α]$_D$: −130.0
¹H-NMR(CDCl₃): δ 3.0 (m, 2H), 3.75 (s, 6H), 3.78 (s, 3H), 3.83-3.99 (m, 1H), 4.34-4.54 (m, 3H), 4.75 (m, 1H), 4.76 (m, 1H), 5.93 (s, 1H), 5.96 (s, 1H), 6.25 (s, 2H), 6.49 (s, 1H), 6.61 (d, 2H, J=8.69 Hz), 6.77 (s, 1H), 7.15 (m, 1H), 7.5 (dd, 1H, J=8.69, 2.64 Hz), 7.88 (m, 3H).
IR(KBr)cm⁻¹: 3334, 2912, 2839, 1774, 1604.
MS (FAB): 640 [M⁺].

EXAMPLE 8

4'-O-Demethyl-4β-[4"-(6"-fluoro-1",3"-benzothiazole-2"-yl)anilino]-4-desoxypodophyllotoxin (4h)

This compound was prepared according to the method described for 4b employing 4-(6-fluoro-1,3-benzothiazole-2-yl)aniline (293 mg, 1.2 mmol) and podophyllotoxin (414 mg, 1 mmol) to get pure product in 60% yield.
m.p: 200-205° C. [α]$_D$: −128.0
¹H-NMR(CDCl₃): δ 3.0 (m, 1H), 3.24 (dd, 1H, J=14.12, 5.2 Hz), 3.7 (s, 6H), 3.8 (t, 1H, J=10.4 Hz), 4.29 (t, 1H, J=7.43 Hz), 4.48 (d, 1H, J=5.2 Hz), 4.82 (m, 1H), 5.9(s, 2H), 6.23 (s, 1H), 6.45 (s, 1H), 6.67 (d, 2H, J=8.92 Hz), 6.75 (s, 1H), 7.1 (m, 1H), 7.52 (dd, 1H, J=8.18, 2.97 Hz), 7.76 (m, 3H).
IR(KBr)cm⁻¹: 3356, 2903, 2834, 1773, 1605.
MS (FAB) 626 [M⁺].

EXAMPLE 9

4β-[4"-(4"-Chloro-1",3"-benzothiazole-2"-yl)anilino]-4-desoxypodophyllotoxin (4i)

This compound was prepared according to the method described for 4a employing 4-(4-chloro-1,3-benzothiazile-2-yl)aniline (312 mg, 1.2 mmol) and podophyllotoxin (414 mg, 1 mmol) to get pure product in 75% yield.
m.p: 136-140° C. [α]$_D$: −117.0
¹H-NMR(CDCl₃): δ 3.01 (m, 2H), 3.76 (s, 6H), 3.8 (s, 3H), 4.37 (m, 2H), 4.53 (m, 1H), 4.75 (m, 1H), 5.93 and 5.97 (ABq, 2H, J=1.51 Hz), 6.26 (s, 2H), 6.5 (s, 1H), 6.59 (d, 2H, J=9.06 Hz), 6.8 (s, 1H), 7.21 (m, 1H), 7.44 (d, 1H, J=8.31 Hz), 7.72 (d, 1H, J=8.31 Hz), 7.96 (d, 2H, J=8.31 Hz).
IR(KBr)cm⁻¹: 3392, 2923, 1773, 1610.
MS (FAB): 657 [M⁺].

EXAMPLE 10

4'-O-Demethyl-4β-[4"-(4"-chloro-1",3"-benzothiazole-2"-yl)anilino]-4-desoxypodophyllotoxin (4j)

This compound was prepared according to the method described for 4b employing 4-(4-chloro-1,3-benzothiazile-2-yl)aniline (312 mg, 1.2 mmol) and podophyllotoxin (414 mg, 1 mmol) to get pure product in 60% yield.
m.p: 155-158° C. [α]$_D$: −124.0
¹H-NMR(CDCl₃): δ 3.08 (m, 2H), 3.8 (s, 6H), 4.35 (m, 2H), 4.6 (d, 1H, J=3.56 Hz), 4.8 (m, 1H), 5.42 (br, 1H), 5.94 and 5.97 (ABq, 2H, J=1.43 Hz), 6.32 (s, 2H), 6.53 (s, 1H), 6.62 (d, 2H, J=8.55 Hz), 6.79 (s, 1H), 7.24 (m, 1H), 7.47 (dd, 1H, J=8.24, 1.43 Hz), 7.74 (dd, 1H, J=8.24, 1.43 Hz), 7.78 (d, 2H, J=8.55 Hz).
IR(KBr)cm⁻¹: 3364, 2925, 1773, 1610.
MS (FAB) 643 [M⁺].

EXAMPLE 11

4β-[4"-(4",6"-Dichloro-1",3"-benzothiazole-2"-yl)anilino]-4-desoxypodophyllotoxin (4k)

This compound was prepared according to the method described for 4a employing 4-(4,6-dichloro-1,3-benzothiazole-2-yl)aniline (354mg, 1.2 mmol) and podophyllotoxin (414 mg, 1 mmol) to get pure product in 70% yield.
m.p: 160-163° C. [α]$_D$: −102.0
¹H-NMR(CDCl₃): δ 3.02 (m, 2H), 3.76 (s, 6H), 3.8 (s, 3H), 4.38 (m, 2H), 4.55 (m, 1H), 4.75 (m, 1H), 5.95 (s, 1H), 5.98 (s, 1H), 6.28 (s, 2H), 6.5 (s, 1H), 6.61 (d, 2H, J=8.3 Hz), 6.79 (s, 1H), 7.48 (s, 1H), 7.71 (s, 1H), 8.95 (d, 2H, J=8.3 Hz).
IR(KBr)cm⁻¹: 3390, 2908, 1773, 1605
MS (FAB): 691 [M⁺]. .

EXAMPLE 12

4'-O-Demethyl-4β-[4"-(4",6'-dichloro-1",3"-benzothiazole-2"-yl)anilino]-4-desoxypodophyllotoxin (4l)

This compound was prepared according to the method described for 4b employing 4-(4,6-dichloro-1,3-benzothiazole-2-yl)aniline (354 mg, 1.2 mmol) and podophyllotoxin (414 mg, 1 mmol) to get pure product in 50% yield.

m.p: 155-158° C. $[\alpha]_D$: −124.0

$^1$H-NMR(CDCl$_3$): δ 3.0-3.77 (m, 2H), 3.79 (s, 6H), 3.88 (m, 1H), 4.34 (m, 1H), 4.54 (m, 1H), 4.86 (m, 1H), 5.38 (br, 1H), 5.98 (s, 2H), 6.32 (s, 2H), 6.53 (s, 1H), 6.73 (d, 2H, J=8.51 Hz), 6.83 (s, 1H), 7.46 (s, 1H), 7.78 (s, 1H), 7.89 (d, 2H, J=8.51 Hz).

IR(KBr)cm$^{-1}$: 3362, 2925, 1774, 1597.

MS (FAB): 677 [M$^+$].

EXAMPLE 13

4β-[4"-(1",3"-Benzothiazole-2"-yl)-2"-bromoanilino]-4-desoxypodophyllotoxin (4m)

This compound was prepared according to the method described for 4a employing 4-(1,3-benzothiazole-2-yl)-2-bromoaniline (366 mg, 1.2 mmol) and podophyllotoxin (414 mg, 1 mmol) to get pure product in 75% yield.

m.p: 125-128° C. $[\alpha]_D$: −90.0

$^1$H-NMR(CDCl$_3$): δ 3.1 (m, 2H), 3.18 (dd, 1H, J=14.6, 4.5 Hz), 3.78 (s, 6H), 3.82 (s, 3H), 4.42 (t, 1H, J=7.57 Hz), 4.68 (d, 1H, J=3.8 Hz), 4.88 (m, 2H), 6.01 (s, 2H), 6.35 (s, 2H), 6.58 (s, 1H), 6.63 (d, 1H, J=8.04), 6.79 (s, 1H), 7.32-7.55 (m, 2H), 7.85-8.1 (m, 3H), 8.29 (d, 1H, J=2.19 Hz).

IR(KBr)cm$^{-1}$: 3394, 2924, 2854, 1776, 1594.

MS (FAB): 703 [M+$^2$].

EXAMPLE 14

4'-O-Demethyl-4β-[4"-(1",3"-benzothiazole-2"-yl)-2"-bromoanilino]-4-desoxypodophyllotoxin (4n)

This compound was prepared according to the method described for 4b employing 4-(1,3-benzothiazole-2-yl)-2-bromoaniline (366 mg, 1.2 mmol) and podophyllotoxin (414 mg, 1 mmol) to get pure product in 60% yield.

m.p: 177-180° C. $[\alpha]_D$: −91.0

$^1$H-NMR(CDCl$_3$): δ 3.13 (m, 2H), 3.81 (s, 6H), 4.4 (t, 1H, J=7.58 Hz), 4.68 (d, 1H, J=3.8 Hz), 4.85 (m, 2H), 5.45 (s, 1H), 6.01 (s, 2H), 6.35 (s, 2H), 6.59 (s, 1H), 6.64 (d, 1H, J=8.04 Hz), 6.79 (s, 1H), 7.32-7.56 (m, 2H), 7.85-8.06 (m, 3H), 8.29 (d, 1H, J=2.26 Hz).

IR(KBr)cm$^{-1}$: 3393, 2923, 2852, 1774, 1598.

MS (FAB): 689 [M+$^2$].

EXAMPLE 15

4β-[4"-(1",3"-Benzothiazole-2"-yl)-2"-methylanilino]-4-desoxypodophyllotoxin (4o)

This compound was prepared according to the method described for 4a employing 4-(1,3-benzothiazole-2-yl)-2-methylaniline (288 mg, 1.2 mmol) and podophyllotoxin (414 mg, 1 mmol) to get pure product in 75% yield.

m.p: 152-155° C. $[\alpha]_D$: −139.0

$^1$H-NMR(CDCl$_3$): δ 2.16 (s, 3H), 3.08 (m, 1H), 3.15 (dd, 1H, J=14.6, 4.4 Hz), 3.78 (s, 6H), 3.82 (s, 3H), 3.9 (t, 1H, J=9.2 Hz), 4.42 (t, 1H, J=7.7 Hz), 4.63 (d, 1H, J=4.2 Hz), 4.85 (m, 1H), 5.98 (s, 2H), 6.32 (s, 2H), 6.56 (s, 1H), 6.8 (s, 1H), 7.1-7.5 (m, 4H), 7.82-8.04 (m, 3H).

IR(KBr): 3411, 2923, 1773, 1607.

MS (FAB): 636 [M$^+$].

EXAMPLE 16

4'-O-Demethyl-4β-[4"-(1",3"-benzothiazole-2"-yl)-2"-methylanilino]-4-desoxypodophyllotoxin (4p)

This compound was prepared according to the method described for 4b employing 4-(1,3-benzothiazole-2-yl)-2-methylaniline (288 mg, 1.2 mmol) and podophyllotoxin (414 mg, 1 mmol) to get pure product in 60% yield.

m.p: 133-135° C. $[\alpha]_D$: −130.0

$^1$H-NMR(CDCl$_3$): δ 2.21 (s, 3H), 3.10 (m, 1H), 3.18 (dd, 1H, J=14.5, 4.5 Hz), 3.8 (s, 6H), 3.9 (t, 1H, J=9.7 Hz), 4.41 (t, 1H, J=7.6 Hz), 4.64 (d, 1H, J=4.2 Hz), 4.88 (m, 1H), 5.45 (s, 1H), 6.0 (d, 2H, J=4.1 Hz), 6.35 (s, 2H), 6.58 (s, 1H), 6.69 (s, 1H), 7.14-7.5 (m, 4H), 7.82-8.05 (m, 3H).

IR(KBr)cm$^{-1}$: 3397, 2907, 1773, 1607.

MS (FAB): 622 [M$^+$].

TABLE 2

| Analogues of podophyllotoxin. | | | |
|---|---|---|---|
| S. No. | R | $R_1$ | $R_2$ |
| 4a | CH$_3$ | H | H |
| 4b | H | H | H |
| 4c | CH$_3$ | 3-Cl | H |
| 4d | H | 3-Cl | H |
| 4e | CH$_3$ | H | 6-OCH$_3$ |
| 4f | H | H | 6-OCH$_3$ |
| 4g | CH$_3$ | H | 6-F |
| 4h | H | H | 6-F |
| 4i | CH$_3$ | H | 4-Cl |
| 4j | H | H | 4-Cl |
| 4k | CH$_3$ | H | 4,6-di-Cl |
| 4l | H | H | 4,6-di-Cl |
| 4m | CH$_3$ | 2-Br | H |
| 4n | H | 2-Br | H |
| 4o | CH$_3$ | 2-CH$_3$ | H |
| 4p | H | 2-CH$_3$ | H |

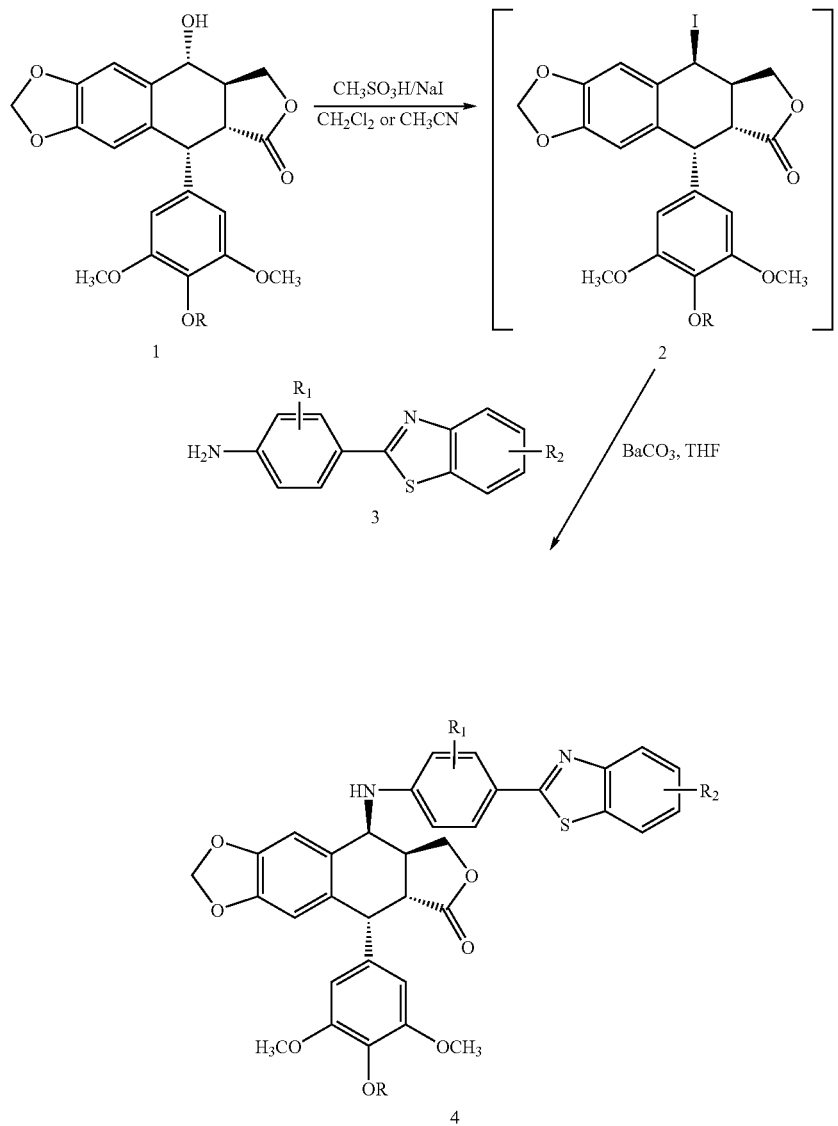

Scheme 1

Biological Activity:

In Vitro Evaluation of Cytotoxic Activity.

Compounds 4a, 4b, 4c, 4d, 4g and 4h have been evaluated for their in vitro cytotoxicity in selected human cancer cell lines i.e., colon (Colo205), lung (Hop-62), cervix (SiHa), prostate (DU145, PC3), oral (DWD, HT1080), and breast (MCF7, Zr-75-1) origin by employing the sulforhodamine B (SRB) assay method (Skehn, P.; Storeng, R.; Scudiero, A.; Monks, J.; McMohan, D.; Vistica, D.; Jonathan, T. W.; Bokesch, H.; Kenney, S.; Boyd M. R. *J. Natl. Cancer Inst.* 1990, 82, 1107). The results (μg/ml) are summarized with podophyllotoxin and standard drug adriamycin in Table-1. All the new compounds were significantly cytotoxic towards the colon and oral cell lines compared to the standard drug tested, with the concentration of the drug that produced 50% inhibition of cell growth ($IC_{50}$).

Procedure of the SRB-assay

Single cell suspension of the tumor cells grown in tissue culture were made, cells counted and cell count adjusted to $1\times10^5$ to $5\times10^5$ cells/ml. Ninety six (96) well plates were seeded with this cell suspension, each well receiving 100 μl of it. The plate was then be incubated at 37° C. temperature in $CO_2$ incubator for 24 hours. Drugs were added at appropriate concentrations after 24-hour incubation followed by further incubation for 48 hours. Experiment was terminated by gently layering the cells in the wells with 30% TCA and plates were kept in refrigerator for 1 hour following which they were washed thoroughly with tap water, dried attained with 0.4% SRB in 1% acetic aid and finally, the bound SRB eluted with 10 mM tris. Absorbance was read at 540 nm, in the microtitre-plate reader. Optical density of drug-treated cells was compared with that of control cells and cell inhibition was calculated as percent values. Each compound was tested at 10, 20, 40 and 80 μg/ml in triplicate on human malignant cell lines.

TABLE 1

Cytotoxicity (in vitro) data for some representative compounds

| | Colon | Prostate | | Lung | Breast | | Cervix | Oral | |
|---|---|---|---|---|---|---|---|---|---|
| Compd. | Colo205 | DU145 | PC3 | Hop62 | MCF7 | Zr-75-1 | SiHa | HT1080 | DWD |
| 4a | 8 | >80 | >80 | >80 | >80 | >80 | >80 | 8 | 22 |
| 4b | 8 | 13 | >80 | 8 | >80 | >80 | >80 | >80 | 6 |
| 4c | 7 | >80 | >80 | 15 | >80 | >80 | >80 | 9 | 5 |
| 4d | 7 | >80 | >80 | 60 | >80 | >80 | >80 | 9 | 7 |
| 4g | 7 | >80 | >80 | 30 | >80 | >80 | >80 | 9 | 5 |
| 4h | 8 | >80 | >80 | 10 | >80 | >80 | >80 | >80 | 9 |
| ADR | 5 | 6 | 5 | 5 | 5 | 5 | 5 | 4 | 2 |
| 1 | 5 | 2 | 8 | 13 | 3 | 7 | 23 | 8 | 6 |

1 = Podophyllotoxin
ADR = Adriamycin is the control drug

Advantages

The main advantages of the present inventions are that these new 4β-[4"-(1",3"-benzothiazole-2"-yl)anilino] analogues of podophyllotoxin have exhibited promising in vitro cytotoxic activity. Further, these compounds have been prepared from podophyllotoxin upon reaction with methanesulphonic acid/NaI followed by the addition of corresponding 4-(1,3-benzothiazole-2-yl)anilines in the presence of $BaCO_3$ at room temperature to provide the 4β-[4"-(1",3"-benzothiazole-2"-yl)anilino]podophyllotoxin analogues in very good yields and in almost stereoselective manner.

We claim:

1. A podophyllotoxin having the following formula 4:

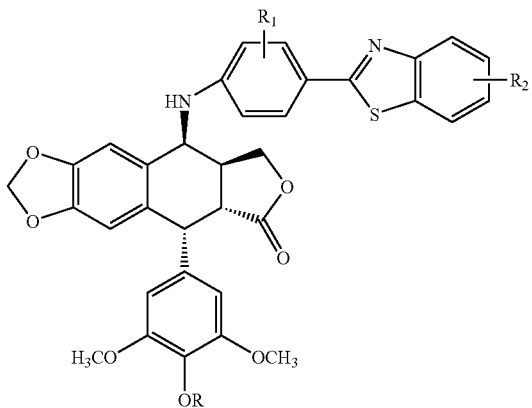

wherein R=H or $CH_3$; $R_1$ is selected from H, halogen and $CH_3$ and $R_2$ is selected from H, halogen and $OCH_3$.

2. A podophyllotoxin according to claim 1 selected from the group consisting of:

4β-[4"-(1", 3"-benzothiazole-2"-yl)anilino]-4-desoxypodophyllotoxin (4a);

4'-O-Demethyl-4β-[4"-(1",3"-benzothiazole-2"-yl)anilino]-4-desoxypodophyllotoxin (4b);

4β-[4"-(1",3"-Benzothiazole-2"-yl)-3"-chloroanilino]-4-desoxypodophyllotoxin (4c);

4'-O-Demethyl-4β-[4"-(1",3"-benzothiazole-2"-yl)-3"-chloroanilino]-4-desoxypodophyllotoxin (4d);

4β-[4"-(6"-Methoxy-1",3"-benzothiazole-2"-yl)anilino]-4-desoxypodophyllotoxin (4e);

4'-O-Demethyl-4β-[4"-(6"-methoxy-1",3"-benzothiazole-2"-yl)anilino]-4-desoxy podophyllotoxin (4f);

4β-[4"-(6"-Fluoro-1",3"-benzothiazole-2"-yl)anilino]-4-desoxypodophyllotoxin (4g);

4'-O-Demethyl-4β-[4"-(6"-fluoro-1",3"-benzothiazole-2"-yl)anilino]-4-desoxypodophyllotoxin (4h);

4β-[4"-(4"-Chloro-1",3"-benzothiazole-2"-yl)anilino]-4-desoxypodophyllotoxin (4i);

4'-O-Demethyl-4β-[4"-(4"-chloro-1",3"-benzothiazole-2"-yl)anilino]-4-desoxypodophyllotoxin (4j);

4β-[4"-(4",6"-Dichloro-1",3"-benzothiazole-2"-yl)anilino]-4-desoxypodophyllotoxin (4k);

4'-O-Demethyl-4β-[4"-(4",6"-dichloro-1",3"-benzothiazole-2"-yl)anilino]-4-desoxypodophyllotoxin (4l);

4β-[4"-(1",3"-Benzothiazole-2"-yl)-2"-bromoanilino]-4-desoxypodophyllotoxin (4m);

4'-O-Demethyl-4β-[4"-(1",3"-benzothiazole-2"-yl)-2"-bromoanilino]-4-desoxypodo-phyllotoxin(4n);

4β-[4"-(1",3"-Benzothiazole-2"-yl)-2"-methylanilino]-4-desoxypodophyllotoxin (4o) and 4'-O-Demethyl-4β-[4"-(1",3"-benzothiazole-2"-yl)-2"-methylanilino]-4-desoxy podophyllotoxin (4p).

3. A podophyllotoxin according to claim 2, wherein the compounds in the group of compounds each have one of the following structural formulae:

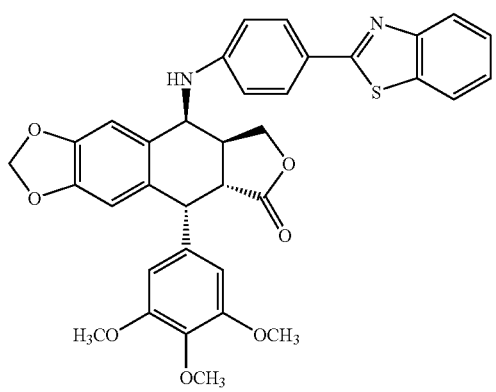

4a

-continued
4b
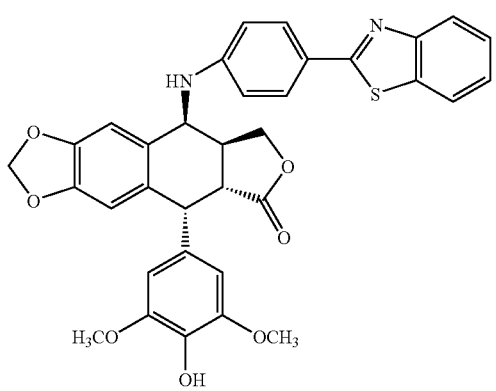
4c
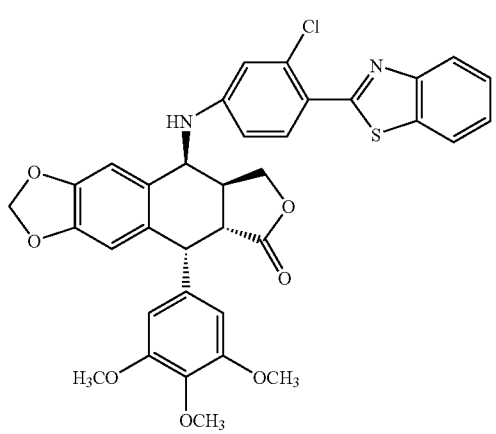
4d
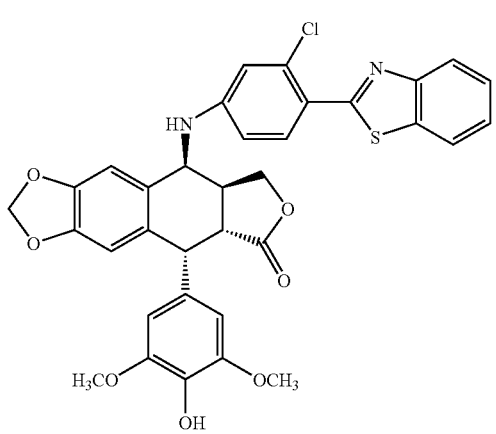
4e
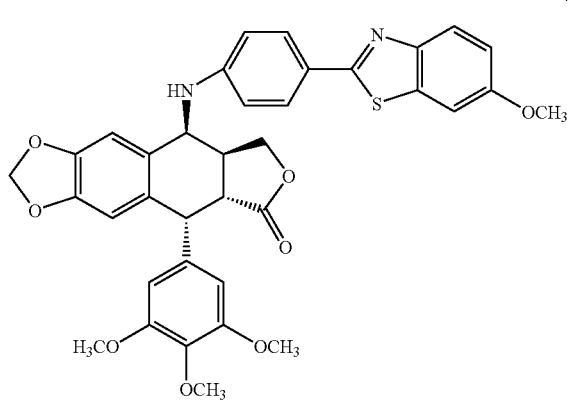
-continued
4f
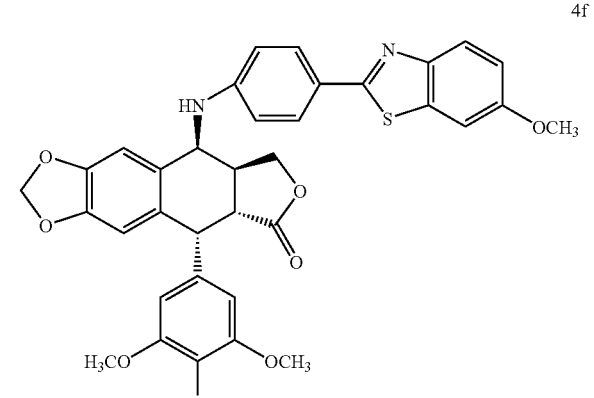
4g
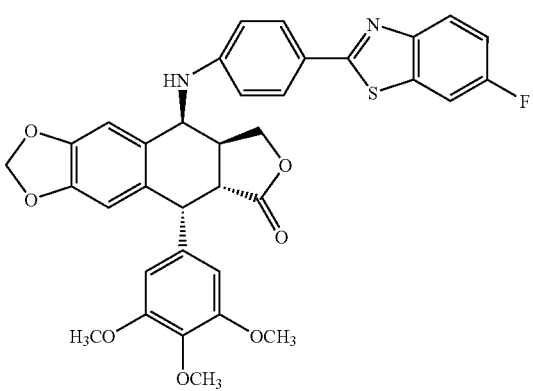
4h
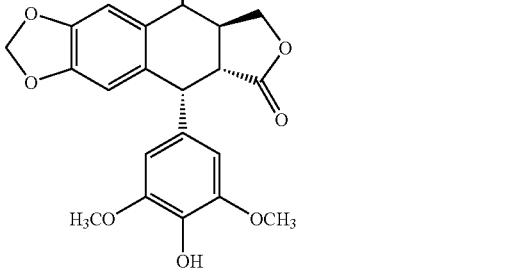
4i
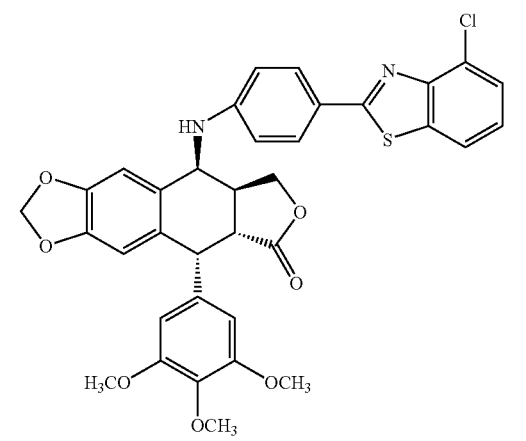

-continued
4j
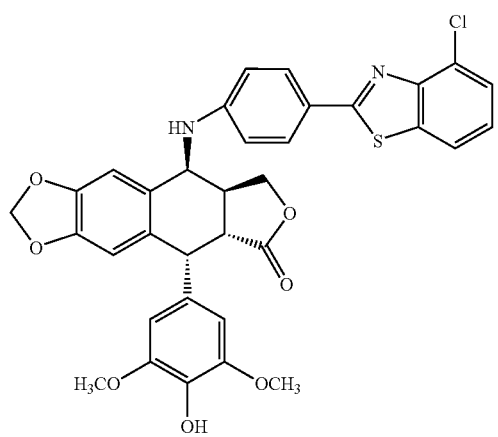
4k
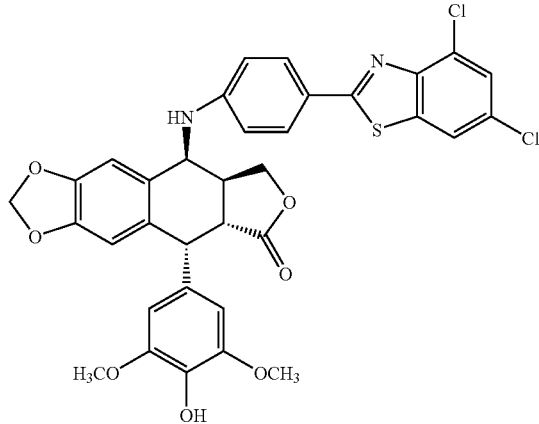
4l
4m
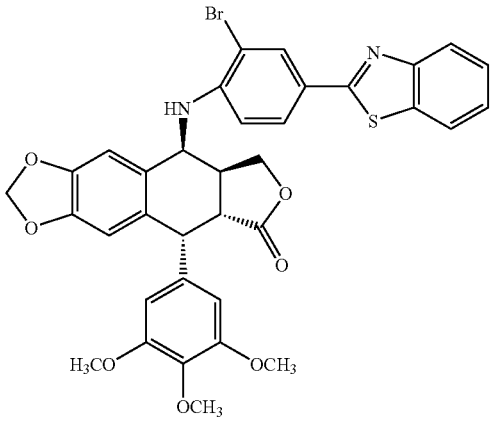
4n
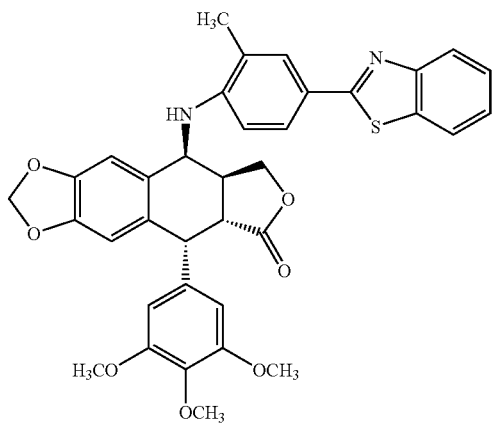
4o

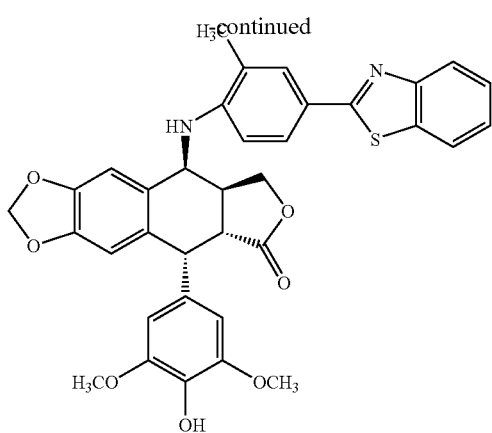

4. A podophyllotoxin according to claim 1 which exhibits in vitro anticancer activity against human cell lines selected from the group consisting of colon cancer cell line Colo205, non small cell lung cancer cell line Hop-62, cervix cancer cell line SiHa, prostrate cancer cell line DU145, prostrate cancer cell line PC3, fibrosarcoma type oral cancer cell line DWD, fibrosarcoma type oral cancer cell line Ht1080, Breast cancer cell line MCF7, and breast cancer cell line Zr-75-1.

5. A podophyllotoxin according to claim 2 which exhibits the following in vitro cytotoxicity data for the compounds indicated towards the cancer cell lines indicated, compared to adriamycin when tested with the concentration that produced 50% inhibition of cell growth ($IC_{50}$):

| | Activity status in terms of $IC_{50}$ values (µg/ml) | | | | | | | | |
|---|---|---|---|---|---|---|---|---|---|
| | Colon | Prostate | | Lung | Breast | | Cervix | Oral | |
| Compd. | Colo205 | DU145 | PC3 | Hop62 | MCF7 | Zr-75-1 | SiHa | HT1080 | DWD |
| 4a | 8 | >80 | >80 | >80 | >80 | >80 | >80 | 8 | 22 |
| 4b | 8 | 13 | >80 | 8 | >80 | >80 | >80 | >80 | 6 |
| 4c | 7 | >80 | >80 | 15 | >80 | >80 | >80 | 9 | 5 |
| 4d | 7 | >80 | >80 | 60 | >80 | >80 | >80 | 9 | 7 |
| 4g | 7 | >80 | >80 | 30 | >80 | >80 | >80 | 9 | 5 |
| 4h | 8 | >80 | >80 | 10 | >80 | >80 | >80 | >80 | 9 |
| ADR | 5 | 6 | 5 | 5 | 5 | 5 | 5 | 4 | 2 |
| 1 | 5 | 2 | 8 | 13 | 3 | 7 | 23 | 8 | 6 | wherein compounds "4a", "4b", "4c", "4d", "4g", and "4h", are the compounds indicated parenthetically in claim 2, "ADR" is adriamycin and compound "1" is podophyllotoxin.

6. A podophyllotoxin according to claim 2 which exhibits in vitro anticancer activity against human cell lines selected from the group consisting of colon cancer cell line Colo205, non-small-cell lung cancer cell line Hop-62, cervix cancer cell line SiHa, prostate cancer cell line DU145, prostate cancer cell line PC3, fibrosarcoma type oral cancer cell line DWD, fibrosarcoma type oral cancer cell line HT1080, breast cancer cell line MCF7, and breast cancer cell line Zr-75-1.

7. A podophyllotoxin according to claim 3 which exhibits in vitro anticancer activity against human cell lines selected from the group consisting of colon cancer cell line Colo205, non-small-cell lung cancer cell line Hop-62, cervix cancer cell line SiHa, prostate cancer cell line DU145, prostate cancer cell line PC3, fibrosarcoma type oral cancer cell line DWD, fibrosarcoma type oral cancer cell line HT1080, breast cancer cell line MCF7, and breast cancer cell line Zr-75-1.

8. A podophyllotoxin according to claim 2 which exhibits the following in vitro cytotoxicity data for the compounds indicated towards cancer cell lines selected from the group consisting of colon cancer cell line Colo205, non-small-cell lung cancer cell line Hop-62, cervix cancer cell line SiHa, prostate cancer cell line DU145, prostate cancer cell line PC3, fibrosarcoma type oral cancer cell line DWD, fibrosarcoma type oral cancer cell line HT1080, breast cancer cell line MCF7, and breast cancer cell line Zr-75-1, compared to adriamycin when tested with the concentration that produced 50% inhibition of cell growth ($IC_{50}$):

| | Activity status in terms of $IC_{50}$ values (µg/ml) | | | | | | | | |
|---|---|---|---|---|---|---|---|---|---|
| | Colon | Prostate | | Lung | Breast | | Cervix | Oral | |
| Compd. | Colo205 | DU145 | PC3 | Hop62 | MCF7 | Zr-75-1 | SiHa | HT1080 | DWD |
| 4a | 8 | >80 | >80 | >80 | >80 | >80 | >80 | 8 | 22 |
| 4b | 8 | 13 | >80 | 8 | >80 | >80 | >80 | >80 | 6 |
| 4c | 7 | >80 | >80 | 15 | >80 | >80 | >80 | 9 | 5 |
| 4d | 7 | >80 | >80 | 60 | >80 | >80 | >80 | 9 | 7 |
| 4g | 7 | >80 | >80 | 30 | >80 | >80 | >80 | 9 | 5 |
| 4h | 8 | >80 | >80 | 10 | >80 | >80 | >80 | >80 | 9 |
| ADR | 5 | 6 | 5 | 5 | 5 | 5 | 5 | 4 | 2 |
| 1 | 5 | 2 | 8 | 13 | 3 | 7 | 23 | 8 | 6 | wherein compounds "4a", "4b", "4c", "4d", "4g", and "4h", are the compounds indicated parenthetically in claim 2, "ADR" is adriamycin and compound "1" is podophyllotoxin.

9. A podophyllotoxin according to claim 3 which exhibits the following in vitro cytotoxicity data for the compounds indicated towards cancer cell lines selected from the group consisting of colon cancer cell line Colo205, non-small-cell lung cancer cell line Hop-62, cervix cancer cell line SiHa, prostate cancer cell line DU145, prostate cancer cell line PC3, fibrosarcoma type oral cancer cell line DWD, fibrosarcoma type oral cancer cell line HT1080, breast cancer cell line MCF7, and breast cancer cell line Zr-75-1, compared to adriamycin when tested with the concentration that produced 50% inhibition of cell growth ($IC_{50}$):

| | | | Activity status in terms of $IC_{50}$ values (µg/ml) | | | | | | |
|---|---|---|---|---|---|---|---|---|---|
| | Colon | Prostate | | Lung | Breast | | Cervix | Oral | |
| Compd. | Colo205 | DU145 | PC3 | Hop62 | MCF7 | Zr-75-1 | SiHa | HT1080 | DWD |
| 4a | 8 | >80 | >80 | >80 | >80 | >80 | >80 | 8 | 22 |
| 4b | 8 | 13 | >80 | 8 | >80 | >80 | >80 | >80 | 6 |
| 4c | 7 | >80 | >80 | 15 | >80 | >80 | >80 | 9 | 5 |
| 4d | 7 | >80 | >80 | 60 | >80 | >80 | >80 | 9 | 7 |
| 4g | 7 | >80 | >80 | 30 | >80 | >80 | >80 | 9 | 5 |
| 4h | 8 | >80 | >80 | 10 | >80 | >80 | >80 | >80 | 9 |
| ADR | 5 | 6 | 5 | 5 | 5 | 5 | 5 | 4 | 2 |
| 1 | 5 | 2 | 8 | 13 | 3 | 7 | 23 | 8 | 6 | wherein compounds "4a", "4b", "4c", "4d", "4g", and "4h", are the compounds indicated by the structural formulae shown in claim 3, "ADR" is adriamycin and compound "1" is podophyllotoxin.

* * * * *